United States Patent
Braun

(10) Patent No.: US 10,038,218 B2
(45) Date of Patent: Jul. 31, 2018

(54) SALTS OF N-CONTAINING HETEROCYCLIC ANIONS AS COMPONENTS IN ELECTROLYTES

(71) Applicant: SOLVAY SA, Brussels (BE)

(72) Inventor: Max Josef Braun, Wedemark (DE)

(73) Assignee: SOLVAY SA, Brussels (BE)

( * ) Notice: Subject to any disclaimer, the term of this patent is extended or adjusted under 35 U.S.C. 154(b) by 432 days.

(21) Appl. No.: 14/653,512

(22) PCT Filed: Dec. 19, 2013

(86) PCT No.: PCT/EP2013/077534
§ 371 (c)(1),
(2) Date: Jun. 18, 2015

(87) PCT Pub. No.: WO2014/096284
PCT Pub. Date: Jun. 26, 2014

(65) Prior Publication Data
US 2016/0197377 A1    Jul. 7, 2016

(30) Foreign Application Priority Data
Dec. 20, 2012   (EP) ..................................... 12198765

(51) Int. Cl.
| | | |
|---|---|---|
| *H01M 10/00* | (2006.01) | |
| *H01M 10/0568* | (2010.01) | |
| *H01M 10/0525* | (2010.01) | |
| *H01M 10/054* | (2010.01) | |
| *H01G 9/20* | (2006.01) | |
| *C07D 231/12* | (2006.01) | |
| *C07D 239/36* | (2006.01) | |
| *H01G 11/62* | (2013.01) | |
| *H01G 11/58* | (2013.01) | |

(52) U.S. Cl.
CPC ...... *H01M 10/0568* (2013.01); *C07D 231/12* (2013.01); *C07D 239/36* (2013.01); *H01G 9/2004* (2013.01); *H01G 9/2013* (2013.01); *H01G 11/58* (2013.01); *H01G 11/62* (2013.01); *H01M 10/054* (2013.01); *H01M 10/0525* (2013.01); H01M 2300/0025 (2013.01); *Y02E 10/542* (2013.01); *Y02E 60/122* (2013.01); *Y02E 60/13* (2013.01)

(58) Field of Classification Search
CPC ........... H01M 10/0525; H01M 10/054; H01M 10/0568; C07D 231/12; C07D 239/36; H01G 9/2004; H01G 11/58
See application file for complete search history.

(56) References Cited

U.S. PATENT DOCUMENTS

| | | | |
|---|---|---|---|
| 6,326,104 B1 * | 12/2001 | Caja | ...................... H01M 6/166 429/188 |
| 6,365,068 B1 | 4/2002 | Michot et al. | |
| 8,431,710 B2 | 4/2013 | Braun | |
| 8,981,115 B2 | 3/2015 | Braun | |
| 2011/0229769 A1 | 9/2011 | Ihara et al. | |
| 2011/0311884 A1 | 12/2011 | Armand | |
| 2012/0222557 A1 | 9/2012 | Schneider et al. | |

FOREIGN PATENT DOCUMENTS

| | | |
|---|---|---|
| JP | 2004-281223 A | 10/2004 |
| WO | 2007093961 A1 | 8/2007 |

OTHER PUBLICATIONS

Chai et al.: "Ether-functionalized pyrazolium ionic liquids as new electrolytes for lithium battery" Electrochimica ACTA vol. 66, 2012, pp. 67-74.
J. Völkl, K. Müller, L. Mokrushina, W. Arlt: "A Priori Property Estimation of Physical and Reactive CO2 Absorbents"Chemical Engineering & Technology Special Issue: Efficient Carbon Capture for Coal Power Plants vol. 35, Issue 3, pp. 579-583, Mar. 2012.
B. Gurkan, B. F. Goodrich, E. M. Mindrup, L. E. Ficke, M. Massel, S. Seo, T. P. Senftle, H. Wu, M. F. Glaser, J. K. Shah, E. J. Maginn, J. F. Brennecke, and W. F. Schneider: "Molecular Design of High Capacity, Low Viscosity, Chemically Tunable Ionic Liquids for CO2 Capture" J. Phys. Chem. Lett., 2010, 1 (24), pp. 3494-3499.

* cited by examiner

*Primary Examiner* — Nicholas P D'Aniello
*Assistant Examiner* — Abibatu O Ojo-Amoo

(57) ABSTRACT

Salts of N-containing heterocyclic anions as components in electrolytes Novel uses of salts of N-containing heterocyclic anions, novel salts of fluorinated N-containing heterocyclic anions and method for producing the same are described. Preferred compounds have a pyrimidone or a pyrazole ring structure bearing a trifluoromethyl group and a metal counter ion.

16 Claims, No Drawings

SALTS OF N-CONTAINING HETEROCYCLIC ANIONS AS COMPONENTS IN ELECTROLYTES

This application is a U.S. national stage entry under 35 U.S.C. § 371 of International Application No. PCT/EP2013/077534 filed Dec. 19, 2013, which claims priority to European application 12198765.5 filed on 20 Dec. 2012. The entire contents of these applications are explicitly incorporated herein by this reference.

The present invention relates to novel uses of salts of N-containing heterocyclic anions, novel salts of fluorinated N-containing heterocyclic anions and method for producing the same. The present invention further concerns an electrolyte comprising salts of N-containing heterocyclic anions and an electrochemical device, in particular a battery and a solar cell, comprising the same.

Chai et al. (Ether-functionalized pyrazolium ionic liquids as new electrolytes for lithium battery, *Electrochimica Acta*, 66, pp. 67-74 (2012)) disclose two salts based on pyrazolium cations and bis(trifluoromethylsulfonyl)imide anions (TFSI$^-$) and their physicochemical and electrochemical properties along with their performances as electrolytes for lithium ion batteries.

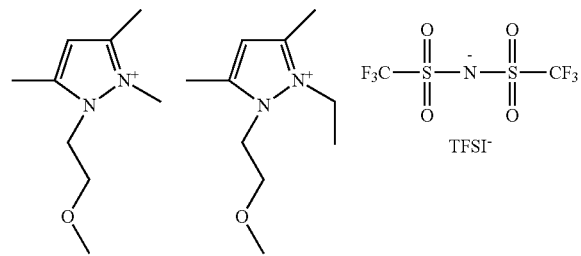

International publication WO 2007/093961 A1 discloses electrolytes comprising salts of tetracyanoborate and an imidazolium cation as components of electrolytes in electrochemical and/or optoelectronic devices, in particular solar cells.

The objective of the present invention is to provide a method of use of salts of N-containing heterocyclic anions, in particular for an electrolyte for electrochemical devices and/or optoelectronic devices. A further objective is to provide novel salts of fluorinated N-containing heterocyclic anions as components in electrolytes. The novel salts may exhibit a high thermal and/or chemical stability. Furthermore, it is an objective of the present invention to provide an electrolyte for electrochemical devices and/or optoelectronic devices that requires the use of less individual compounds in the electrolyte mixture. The method of use and the salts of the present invention can provide advantages like improving the viscosity or reducing the flammability of the electrolytes. Another advantage is the modification of the electrodes under formation of beneficial films. Furthermore, the compounds of the invention advantageously lead to a better wettability of the separator.

These objectives, and other objectives, are achieved by the invention as outlined in the description and the claims.

The present invention therefore relates to a method of use of a compound of general formula I

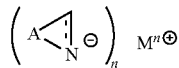

or any tautomer thereof, wherein A is a linking group comprising 3 or 4 annular atoms independently selected from C, N, O or S and wherein $M^{n\oplus}$ is a cation and n is 1, 2, 3 or 4; as a component in an electrolyte. Preferably the electrolyte is used in a lithium ion battery, a sodium ion battery, a superconductor or an organic photovoltaic device.

"Annular" as used herein is meant to denote a group of atoms that form part of the ring structure of the compound. For example, a group A with 3 annular atoms leads to a compound of general formula I with a five-membered ring structure.

"Cation" as used herein is intended to denote an atom or a molecule that has a positive charge. Examples of advantageous cations are metal ions, sulfonium $S^+R_3$, wherein R can independently be selected from alkyl, alkenyl or aryl, phosphonium $P^+R4$, wherein R can independently be selected from alkyl, alkenyl or aryl, ammonium $N^+R4$, wherein R can independently be selected from alkyl, alkenyl or aryl, and N-containing heterocyclic, preferably imidazolilium, more preferably 3-methylimidazolium, or a pyrazolium, more preferably a fluorinated pyrazolium, yet more preferably a 3-$CF_3$-pyrazolium, or any combination thereof. Further examples of advantageous cations comprise uronium, thiouronium, guanidinium, iodonium and other heterocyclic cations such as pyridinium, quinolinium, isoquinolinium, piperazinium, piperidinium, pyrrolium, pyrizinium, indolium, quinoxalinium, thiomorpholinium, morpholinium, and indolinium cations.

The use of metal ions, especially the use of Na$^+$, Li$^+$, or Zn$^{2+}$ has been found to be especially advantageous.

The term "alkyl group" is intended to denote an optionally substituted chain of saturated hydrocarbon-based groups, such as, in particular, a C1-C6 alkyl. By way of example, mention may be made of methyl, ethyl, propyl, isopropyl, butyl, t-butyl, pentyl, isopentyl and hexyl.

The term "alkenyl group" is intended to denote an optionally substituted chain of carbon atoms, wherein at least two of the carbon atoms being bonded together chemically by means of a double bond. Examples of alkenyl include ethenyl (vinyl), 1-propenyl, 2-propenyl, 1-butenyl The term "aryl group" is intended to mean an optionally substituted group which derives from an aromatic nucleus such as, in particular, a C6-C10 aromatic nucleus, in particular phenyl or naphthyl.

The invention further relates to compounds of general formula I

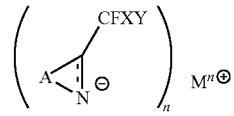

or any tautomer thereof, wherein A is a linking group comprising 3 or 4 annular atoms independently selected from C, N, O or S; wherein X and Y are independently selected from the group consisting of H, alkyl, F and Cl; and wherein M is a metal cation and n is 1, 2, 3 or 4; and their use as a component in an electrolyte.

In a preferred aspect A is —C(O)N=CH—CH= and the compound is

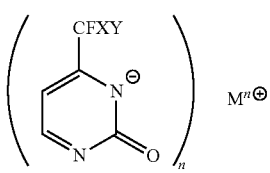

or any tautomer thereof.

In another preferred aspect A is —N=CH—CH= and the compound is

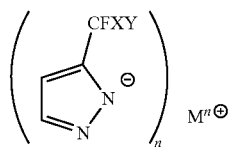

or any tautomer thereof.

In another preferred aspect M is Li, Na or Zn.

In another preferred aspect, —CFXY is —CF$_3$, —CHF$_2$, or —CClF$_2$, more preferably —CF$_3$.

The salts of N-containing heterocyclic anions as described herein can be used as conductive salt and/or solvent and/or solvent additive in electrolytes.

In another embodiment, the salts of N-containing heterocyclic anions as described herein can be used as solid electrolytes, preferably as solid electrolytes in sodium, lithium or zinc ion batteries, especially preferred in lithium ion batteries. In this embodiment, they can be used as such or as mixture with other compounds to form the solid electrolyte. Use of a solid electrolyte according to the invention could enable high-energy battery chemistries. Additionally, it could circumvent safety issues associated with the use of liquid electrolytes.

The invention further relates to an electrolyte containing a compound as described above and at least one other component, preferably the at least one other component is a conductive salt, a solvent and/or a solvent additive.

The compounds of the present invention can be present in a concentration in the electrolyte of 0.25 to 2.5 mol/l, preferably 0.5 to 1.5 mol/l, more preferably 0.9 to 1.1 mol/l.

In certain embodiments, the electrolyte according to the present invention further comprises at least one conducting salt, preferably a Li salt, more preferably LiPF$_6$, LiPO$_2$F$_2$, LiBF$_4$, LiB(CN)$_4$, LiAsF$_6$, LiClO$_4$, LiBOB (lithium bisoxalatoborate), LiFSI (lithium bis(fluorosulfonyl)imidide), LiTFSI (lithium bis(trifluoromethylsulfonyl)imidide), LiN(CF$_3$SO$_2$)$_2$), LiBeti (lithium bis(perfluoroethylsulfonyl)imidide), LiODBF (LiBF$_2$C$_2$O$_4$), LiB(C$_6$H$_5$), LiCF$_3$SO$_3$, LiC(CF$_3$SO$_2$)$_3$, and any combination thereof, more preferably LiPF$_6$, LiPO$_2$F$_2$, or LiTFSI. In another preferred embodiment the electrolyte further comprises a conducting salt, more preferably LiPF$_6$. Often, the concentration of the further conducting salt is 0.5 to 1.5 mol/l, more preferably 0.9 to 1.1 mol/l.

In certain embodiments, the electrolyte according to the present invention further comprises at least one suitable solvent, preferably an organic carbonate, lactone, formamide, pyrrolidinone, oxazolidinone, nitroalkane, N,N-substituted urethane, sulfolane, dialkyl sulfoxide, dialkyl sulfite, acetate, nitrile, acetamide, glycol ether, dioxolane, dialkyloxyethane, or trifluoroacetamide.

Preferably, the suitable solvent is a dialkyl carbonate, alkylene carbonate, ketone or formamide, dimethyl formamide, carboxylic acid amide, acetone, acetonitrile, dimethyl carbonate, diethyl carbonate, methyl ethyl carbonate, cyclic alkylene carbonates, e.g. ethylene carbonate, propylene carbonate or vinylidene carbonate.

In certain embodiments, the electrolyte according to the present invention further comprises at least one solvent additive selected from fluorosubstituted ethylene carbonates, polyfluorosubstituted dimethyl carbonates, fluorosubstituted ethyl methyl carbonates, fluorosubstituted diethyl carbonates, mono fluoroethylene carbonate, 4,4-difluoro ethylene carbonate, 4,5-difluoro ethylene carbonate, 4-fluoro-4-methyl ethylene carbonate, 4,5-difluoro-4-methyl ethylene carbonate, 4-fluoro-5-methyl ethylene carbonate, 4,4-difluoro-5-methyl ethylene carbonate, 4 (fluoromethyl)-ethylene carbonate, 4-(difluoromethyl)-ethylene carbonate, 4 (trifluoromethyl)-ethylene carbonate, 4-(fluoromethyl)-4-fluoro ethylene carbonate, 4-(fluoromethyl)-5-fluoro ethylene carbonate, 4-fluoro-4,5-dimethyl ethylene carbonate, 4,5-difluoro-4,5-dimethyl ethylene carbonate, and 4,4 difluoro-5,5-dimethyl ethylene carbonate, fluoromethyl methyl carbonate, difluoromethyl methyl carbonate, trifluoromethyl methyl carbonate, bis(difluoro)methyl carbonate, and bis (trifluoro)methyl carbonate; ethyl methyl carbonate derivatives including 2-fluoroethyl methyl carbonate, ethyl fluoromethyl carbonate, 2,2-difluoroethyl methyl carbonate, 2-fluoroethyl fluoromethyl carbonate, ethyl difluoromethyl carbonate, 2,2,2-trifluoroethyl methyl carbonate, 2,2-difluoroethyl fluoromethyl carbonate, 2-fluoroethyl difluoromethyl carbonate, and ethyl trifluoromethyl carbonate; and diethyl carbonate derivatives including ethyl (2-fluoroethyl) carbonate, ethyl (2,2 difluoroethyl) carbonate, bis(2-fluoroethyl) carbonate, ethyl (2,2,2 trifluoroethyl) carbonate, 2,2-difluoroethyl 2'-fluoroethyl carbonate, bis(2,2-difluoroethyl) carbonate, 2,2,2-trifluoroethyl 2'-fluoroethyl carbonate, 2,2,2-trifluoroethyl 2',2'-difluoroethyl carbonate, and bis(2,2,2-trifluoroethyl) carbonate, 4-fluoro-4-vinylethylene carbonate, 4-fluoro-5-vinylethylene carbonate, 4,4-difluoro-4-vinylethylene carbonate, 4,5-difluoro-4-vinylethylene carbonate, 4-fluoro-4,5-divinylethylene carbonate, 4,5-difluoro-4,5-divinylethylene carbonate, 4-fluoro-4-phenylethylene carbonate, 4-fluoro-5-phenylethylene carbonate, 4,4-difluoro-5-phenylethylene carbonate, 4,5-difluoro-4-phenylethylene carbonate and 4,5 difluoro-4,5-diphenylethylene carbonate, fluoromethyl phenyl carbonate, 2-fluoroethyl phenyl carbonate, 2,2-difluoroethyl phenyl carbonate and 2,2,2 trifluoroethyl phenyl carbonate, fluoromethyl vinyl carbonate, 2 fluoroethyl vinyl carbonate, 2,2-difluoroethyl vinyl carbonate and 2,2,2 trifluoroethyl vinyl carbonate, fluoromethyl allyl carbonate, 2 fluoroethyl allyl carbonate, 2,2-difluoroethyl allyl carbonate and 2,2,2 trifluoroethyl allyl carbonate.

Most preferred is a solvent from the list consisting of ethylene carbonate, dimethyl carbonate, propylene carbonate, diethyl carbonate, 1,2-dimethoxyethane, γ-butyrolactone or a mixture thereof, especially preferred is a 1:2 (v/v) mixture of ethylene carbonate and dimethyl carbonate.

In certain embodiments, the solvents as described herein can also serve as solvent additives or the solvent additives as described herein can serve as solvents.

The present invention still further relates to electrochemical devices and/or optoelectronic devices comprising the salts of N-containing heterocyclic anions or the electrolytes according to the present invention. The electrochemical device and optoelectronic device, respectively, can be selected from batteries and solar cells. Preferred devices are selected from the group consisting of lithium ion battery, sodium ion battery, zinc ion battery, supercapacitor or hybrid supercapacitor, or organic photovoltaic device or dye-sensitized solar cell (DSSC).

The compounds of the invention can be advantageously prepared from the corresponding N-containing heterocycles by salt formation with a suitable base. Examples for suitable bases for the preparation of metal salts are LiOH, LiH, butyl lithium, $Li_2O$, NaOH, NaH, $Na_2O$, ZnO, or $Zn(OH)_2$. The water formed in cases a hydroxide or oxide salt is used can advantageously be removed from the mixture by means of azeotropic or hetero-azeotropic distillation, preferably using a Dean-Stark apparatus. Alternatively, the compounds of the present invention can be prepared by salt exchange, for example by reaction of lithium salts of N-containing heterocyclic anions with a chloride salt of the required cation in a suitable aprotic solvent, removal of the lithium chloride formed by filtration and distillation of the aprotic solvent.

Suitable solvents for the preparation of the salts are aprotic organic solvents, preferably hydrocarbons, aromatic hydrocarbons, dimethylsulfoxide, dimethylformamide, dimethylacetamide, acetonitrile or halogenated hydrocarbons, more preferably aromatic hydrocarbons, especially toluene or benzene.

Should the disclosure of any patents, patent applications, and publications which are incorporated herein by reference conflict with the description of the present application to the extent that it may render a term unclear, the present description shall take precedence.

The invention will now be further described in examples without intending to limit it.

EXAMPLES

Synthesis of the lithium salt of 2-oxo-6-(trifluoromethyl)pyrimidone

A sample of 2-oxo-6-(trifluoromethyl)pyrimidine-2-one (prepared according to WO 2010/037688) was dissolved in toluene and 1 equivalent dry lithium hydroxide was added as a solid. The resulting mixture was heated using a Dean-Stark apparatus. After no more water was removed from the mixture, the toluene was distilled off at 60° C. and a pressure of 100 mbar. A solid was obtained that was kept under argon.

Preparation of Electrolytes

The electrolyte composition is prepared by addition of the lithium salt of 2-oxo-6-(trifluoromethyl)pyrimidone in a concentration of 1 mol/l to the a 1:2 (v/v) mixture of ethylene carbonate and dimethyl carbonate under nitrogen atmosphere.

Direct Preparation of Pyrazole Electrolyte 3-trifluormethyl-1H-pyrazole (2 mol/l) is dissolved in 100 ml 1,2-dimethoxyethane under nitrogen. Lithium hydride (1 eq) is added to the solution. After the evolution of hydrogen ceases, 100 ml ethylene carbonate is added to the solution.

The invention claimed is:

1. An electrolyte comprising a compound of formula

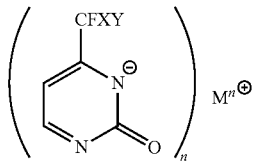

or of formula

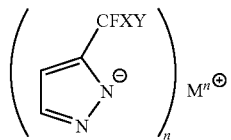

or any tautomer thereof;
wherein X and Y are independently selected from the group consisting of H, alkyl, F and Cl; and wherein $M^{n\oplus}$ is a cation and n is 1, 2, 3 or 4.

2. The electrolyte of claim 1, wherein M is a metal.

3. A lithium ion battery, a sodium ion battery, a supercapacitor or hybrid supercapacitor, or an organic photovoltaic device comprising the electrolyte according to claim 1.

4. A superconductor comprising the electrolyte according to claim 1.

5. A compound of formula

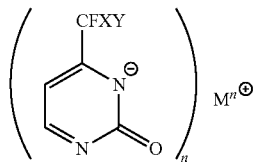

or of formula

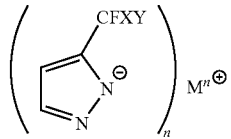

or any tautomer thereof,
wherein X and Y are independently selected from the group consisting of H, alkyl, F and Cl; and
wherein $M^{n\oplus}$ is a metal cation and n is 1, 2, 3 or 4.

6. The compound of claim 5, wherein —CFXY is $CF_3$, —$CHF_2$, or —$CClF_2$.

7. The compound of claim 6 wherein —CFXY is —$CF_3$.

8. The compound of claim 5, wherein M is Li, Na or Zn.

9. An electrolyte comprising the compound of claim 5 and at least one other component.

10. A lithium ion battery, a sodium ion battery, a zinc ion battery, a supercapacitor or hybrid supercapacitor, or an organic photovoltaic device comprising the electrolyte of claim 9.

11. The electrolyte of claim 1, further comprising at least one other component.

12. The electrolyte of claim 11, wherein the at least one other component is selected from the group consisting of a conductive salt, a solvent, and a solvent additive.

13. The electrolyte of claim 9, wherein the at least one other component is selected from the group consisting of a conductive salt, a solvent, and a solvent additive.

14. The compound of claim 7, wherein M is Li.

15. The electrolyte of claim 1, wherein the compound is the lithium salt of 2-oxo-6-(trifluoromethyl)pyrimidone or the lithium salt of 3-trifluoromethyl-1H-pyrazole.

16. The compound of claim 5, wherein the compound is the lithium salt of 2-oxo-6-(trifluoromethyl)pyrimidone or the lithium salt of 3-trifluoromethyl-1H-pyrazole.

\* \* \* \* \*